United States Patent [19]
Lemaitre et al.

[11] Patent Number: 5,658,301
[45] Date of Patent: Aug. 19, 1997

[54] SELF-CENTERING VALVULOTOME

[75] Inventors: George D. Lemaitre, Andover; George W. Lemaitre, Charlestown; Fernando Alvarez de Toledo, Concord, all of Mass.

[73] Assignee: Vascutech, Inc., Burlington, Mass.

[21] Appl. No.: 427,808

[22] Filed: Apr. 26, 1995

[51] Int. Cl.⁶ .................................................. A61B 17/32
[52] U.S. Cl. .................................... 606/159; 606/170
[58] Field of Search ............................... 606/159, 167, 606/170; 604/167, 22

[56] References Cited

U.S. PATENT DOCUMENTS

| | | | |
|---|---|---|---|
| 3,837,345 | 9/1974 | Matar | 606/159 |
| 5,069,679 | 12/1991 | Taheri | 606/159 |
| 5,133,725 | 7/1992 | Quadi | 606/159 |
| 5,152,771 | 10/1992 | Sebbaghian et al. | 606/159 |
| 5,156,610 | 10/1992 | Reger | 606/159 |
| 5,171,316 | 12/1992 | Mehigan | 606/159 |
| 5,234,450 | 8/1993 | Segalowitz | 606/159 |
| 5,269,764 | 12/1993 | Vetter et al. | 604/167 |
| 5,282,484 | 2/1994 | Reger | 128/898 |
| 5,304,189 | 4/1994 | Goldberg et al. | 606/159 |
| 5,352,232 | 10/1994 | Cohen | 606/159 |

*Primary Examiner*—Michael Buiz
*Assistant Examiner*—Patrick W. Rasche
*Attorney, Agent, or Firm*—Timothy J. Shea, II

[57] ABSTRACT

Self-centering valvulotome (V) having a flexible cable (1) partly and slidably disposed within a protective sheath (2), a cutting unit (4), having at least three radially mounted, retractable cutting blades, attached to the cable at its distal end, and a dual-purpose control mechanism attached to the cable at its proximal end. Each retractable cutting blade comprises a free-floating cutting head and a flat spring section, which biases the cutting head against the venous wall. The control mechanism comprises a T-valve segment disposed partly within the proximal end of the protective sheath. A pull handle affixed to the proximal end of the cable can engage the T-valve such that a fluid-tight seal is created, thereby allowing the introduction of a diagnostic or therapeutic fluid to the protective sheath via an access port in the valve.

17 Claims, 3 Drawing Sheets

SELF-CENTERING VALVULOTOME

FIELD OF THE INVENTION

The present invention relates to a blood vessel instrument with self-centering structure and more particularly to a self-centering valvulotome and method of use thereof during certain medical procedures including in situ arterial bypass surgery.

BACKGROUND OF THE INVENTION

In order to allow the arterial-like free flow of blood through a vein selected for use as an arterial bypass, the surgeon must first disable the vein's valves. The procedure is best accomplished by severing the valves with a valvulotome.

A common problem encountered by vascular surgeons is the restriction of arterial blood flow in the lower extremities. Such restriction usually results from atherosclerotic occlusive disease. If left untreated, tissue necrosis inevitably results, usually requiring amputation of the limb. A favored method of restoring proper arterial blood flow is in situ arterial bypass surgery.

Veins return blood to the heart; venous blood in the lower extremities must overcome the force of gravity to continue its journey to the heart. In addition, venous return flow is not aided by the pressure exerted by contraction of the heart to the extent that arterial flow is so aided. To accomplish the difficult task of returning blood to the heart from the lower extremities, veins have developed specialized strategies.

Both veins and arteries are composed of three layers: an outer connective tissue layer with numerous fibers, a middle layer of smooth muscle, and an inner layer of connective tissue lined with simple squamous endothelium. However, unlike the arterial wall, the venous wall is easily collapsible, as the smooth muscle layer in veins is much less developed, and the connective tissue layer is thicker, than in arteries. Because venous walls easily collapse, contraction of the surrounding skeletal muscles squeezes the veins, thereby creating pressure on the venous blood, just as contraction of the heart creates pressure on arterial blood. This externally generated pressure on venous blood would not result in the blood's return to the heart if veins did not have some mechanism to inhibit retrograde blood flow.

Nature has provided an elegant solution to this problem: one-way valves arranged so that blood will easily flow toward the heart and not reverse course when skeletal muscular contractions squeeze the vein. These valves are actually two semicircular flaps formed from the vein's interior endothelial lining. However, while the valves are necessary for proper venous blood flow, they are no longer desirable when a vein segment is to be used as an arterial bypass to revascularize a limb.

It is, by now, a well-known surgical technique to remove a vein segment from a limb and reversing its direction upon reimplantation so the valves will allow blood to flow away from the heart. However, this solution has created significant problems. First, because blood vessels naturally taper the farther they are from the heart, an inverted bypass segment has its narrower end connected to the wider end of the artery and vice versa. This anomalous structure can create undesirably turbulent blood flow that may be linked to the development of intimal hyperplasia. Second, during the surgical procedure, veins are quite sensitive to handling, lack of blood, and lowered temperature. These trauma can lead to strong contractions resulting in severe venospasms. Finally, the open wounds necessary for this procedure can result in painful, swollen, erythematous, and, often, necrotic wounds.

In response to these drawbacks of the reversed grafting technique, surgeons developed the in situ bypass procedure. This procedure allows the surgeon to revascularize the limb without removing the bypass vein from its natural position. Because the vein will retain its natural orientation, the turbulent blood flow associated with inverted veins is avoided. Also, because the vein is minimally handled and not removed from its natural environment, the incidence of severe venospasms is reduced. Finally, because the leg is not required to be laid open, wound necrosis is minimized. However, there remains the problem of the wrong-way valves.

The preferred solution to this problem is to disable the valves using a valvulotome. Valvulotomes are medical catheters that are inserted into the vein and destroy venous valves, thereby enabling the vein to be used as an arterial bypass. The devices comprise a cable having a head unit sized to fit the diameter of the saphenous vein selected for the bypass. The head unit is usually a blunted cylinder having a rearward-facing cutting blade that shreds the valves when the surgeon withdraws the valvulotome from the vein. The extant devices most similar to this invention are the LeMaitre® valvulotome and the valvulotome disclosed in U.S. Pat. No. 5,152,771 to Sabbaghian et al. Neither of these devices reads on the presently claimed invention.

My prior invention of circa 1983, the LeMaitre® retrograde valvulotome (made and sold by Vascutech, Inc.), has become an industry standard. It comprises a tapered head unit with a recessed blade and a tapered follower attached to a cable. To perform the valvulotomy, the surgeon inserts the valvulotome into the saphenous vein selected for the bypass and works the head to a locus just above the first valve to be severed. Upon withdrawal of the valvulotome by the surgeon, the follower opens the collapsed vein to its proper diameter, protecting the vein from the recessed cutting blade. There is enough space between the follower and the cutting blade for the valve to return to its normal closed position, whereafter the cutting blade shears the valve, rendering it inoperative.

However, despite its technical and commercial success, the above-described retrograde valvulotome, as implemented in the present state of the art, does pose several difficulties. First, the surgeon must select an appropriate size valvulotome based upon the vein selected for the bypass. Yet, because the vein naturally expands the farther one goes toward the heart, a valvulotome that is appropriate for the more distal point where the valvulotome is inserted into the vein is often too small for the portion of the vein lying closer to the heart. Thus, for valves significantly "upstream" of the insertion point, the surgeon must turn the valvulotome in order to bias the cutting blade against the portion of the valve closest to the vein wall and ensure that both sides or cusps of the valve are disabled. As can be imagined, success depends greatly upon the surgeon's technique and experience; as often a 2 mm instrument attempts to cut a 6 mm valve. Second, a safety feature is needed whereby the cutting blade can be retracted or sheathed to protect the vein wall if the need arises. Finally, ways are needed for fluid insertion or removal at or near the cutting head and to allow for fluid pressure monitoring at that site by the surgeon during the procedure.

The Sabbaghian valvulotome comprises an orthogonal blade assembly for cutting the venous valves, a shaft for guiding the blade assembly through the bypass vein, an expansion means for preventing the blade assembly from contacting the walls of the bypass vein, and a control means for controlling the expansion and contraction of the expansion means. Although the inventor of this device claims it to be useful in a variety of bypass vein diameter sizes, the surgeon still must control the degree of cutting blade bias against the vein wall. Since veins naturally taper, this places a burden on the surgeon to precisely control the cutting blades, lest the vein wall be damaged or even punctured. However, less than 20% of in situ procedures are performed using an angioscope, which allows the surgeon to visually reference the interior of the vein. Thus, typically, the surgeon has no way of determining the diameter of the vessel at a given point and thus, the precise location of the vein wall. Accordingly, any positional adjustments made by the surgeon are guesses at best.

The ideal valvulotome should effectively, efficiently, and automatically disable the valves, yet not damage the vein wall. Accordingly, it is desirable that the valvulotome be self-centering to minimize the incidence of injuries to the venous wall due to physician error. In addition to enabling precise cutting blade control, the ideal valvulotome should be able to provide optimal results regardless of the size of the vein lumen. This is best achieved by having the cutting blades automatically bias against the vein wall. Further, the ideal valvulotome should have a safety feature whereby the cutting blade can be retracted or sheathed to protect the vein wall if the need arises. Finally, the ideal valvulotome should allow for fluid insertion or removal at or near the cutting head and also should allow for fluid pressure monitoring at that site by the surgeon during the procedure.

The present invention provides an elegant solution to all of the problems associated with conventional valvulotomes and is the closest approximation yet of an ideal valvulotome.

A principal object of the present invention is to provide a self-centering means for optimally severing venous valve flaps regardless of the vein lumen diameter.

Another object of the present invention is to provide such a valve-severing means that does not pose a significant risk of patient injury due to variations in physician skill and expertise.

Yet another object of the present invention is to provide a valve-severing means whereby the cutting blade can be retracted or sheathed to protect the vein wall if the need arises.

A still further object of the present invention is to provide a valve-severing means that allows for fluid insertion or removal at or near the cutting head and that also allows for fluid pressure monitoring at that site by the surgeon during the procedure.

SUMMARY OF THE INVENTION

The present invention, meeting the foregoing objects, comprises a self-sizing valvulotome, and method of use thereof during in situ arterial bypass surgery. The invention in its broadest aspects is also applicable to a wide range of instruments and procedures.

The valvulotome comprises a flexible cable partly and slidably disposed within a protective sheath. A cutting unit is attached at one end of the cable and a pull handle is attached at the opposite end. The cutting head has a base, at least three equally radially mounted, retractable cutting blades attached to the base, and a tip capable of accommodating the cutting blades. Each retractable cutting blade has a first end that is attached to the base, a second, unattached end defining a cutting head, and a self-sizing, self-centering arm disposed therebetween. Each cutting blade is constructed so that the self-sizing, self-centering arm extends outward in a radial direction relative to the cable such that, during use, the radial distance separating the outermost point of each self-sizing, self-centering arm from the cable is greater than the radial distance separating the outermost point of each cutting blade from the cable. Each cutting head has an upper, non-cutting outermost edge shielding a cutting edge disposed inwardly therefrom relative to the cable such that the cutting edge is oriented toward the end of the cable having the pull handle. The cutting head is constructed so that the venous valve is opened upon insertion of the valvulotome, but that the vein's natural bloodflow is allowed to close the valve once the cutting head has passed through, maximizing the destruction of the valve flaps when the cutting head is withdrawn through the valve. The protective sheath is flared outward at the distal end to accommodate the cutting head; a control mechanism that can engage the pull handle is attached at the proximal end.

The surgeon can sheathe and unsheathe the cutting head by sliding the flexible cable distally or proximally relative to the protective sheath. When the pull handle engages the control mechanism, a fluid-tight seal is created, thereby allowing the introduction of a diagnostic or therapeutic fluid to the distal rind of the protective sheath via an access port in the control mechanism and the lumen of the protective sheath.

To prepare a vein for in situ arterial bypass surgery, the surgeon first selects a suitable vein for the procedure, accesses the vein at both a distal and a proximal point, and segments it thusly. Next, a valvulotome of the present invention is inserted into the vein segment at its distal access point and is fed into the vein segment until the cutting unit is past the most proximal valve in the vein segment. The surgeon then unsheathes the cutting unit and withdraws the valvulotome from the vein segment, thereby severing each valve in the segment.

To measure fluid pressure in a vessel, the surgeon accesses the vessel in at least one point, inserts a valvulotome of the present invention into the vessel via the access point, and feeds the valvulotome into the vein segment until the cutting unit is at the point where fluid pressure readings are desired. A fluid pressure measurement device is attached to the control mechanism's access port and the fluid pressure is measured at the desired point.

To introduce fluid into or withdraw fluid from a vessel, the above method is repeated, feeding the valvulotome into the vessel until the cutting unit is at the point where fluid is desired to be added or withdrawn. Then, a diagnostic or therapeutic fluid is introduced into the vessel at the distal end of the protective sheath via the control mechanism's access port and the lumen of the protective sheath, or, alternatively, fluid is withdrawn from the vessel through the distal end of the protective sheath via the protective sheath's lumen and the access port.

Other objects, features and advantages will be apparent from the following detailed description of preferred embodiments thereof taken in conjunction with the accompanying drawings in which:

DESCRIPTION OF PREFERRED EMBODIMENTS

Figure 1:
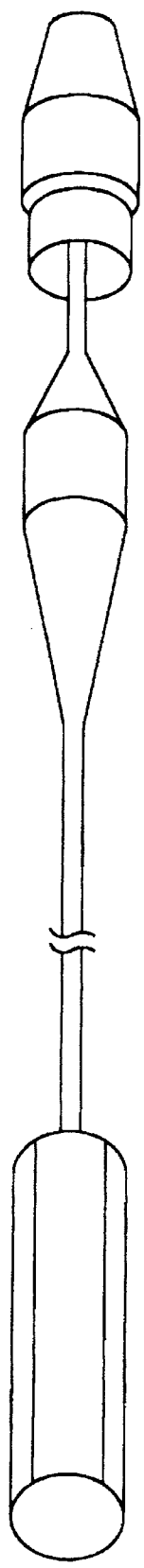
FIG. 1 (Prior Art) is a schematic view of a valvulotome of my prior invention.
Figure 2:
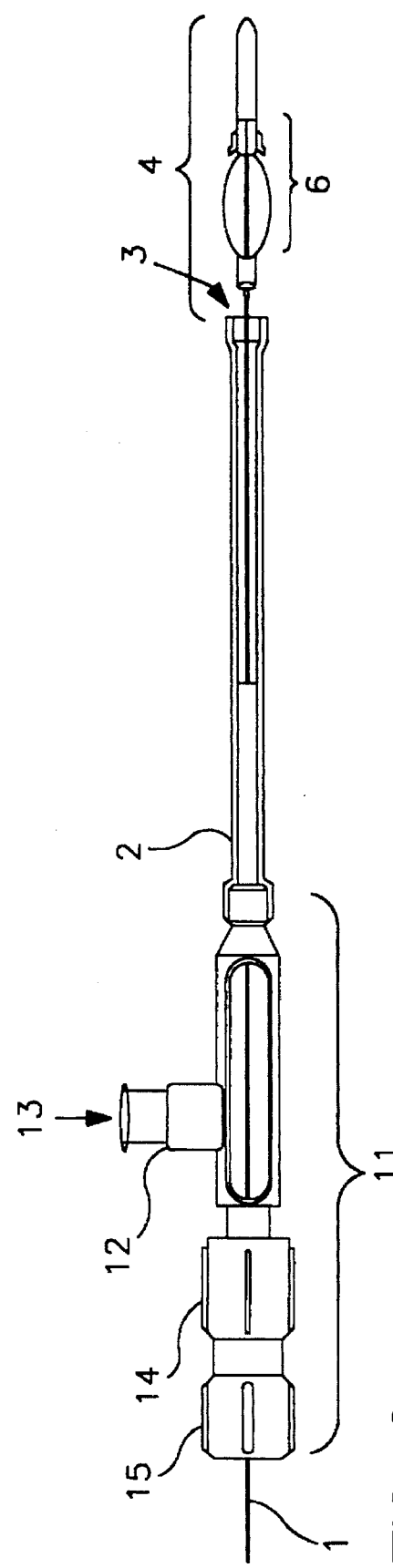
FIG. 2 is a side view of a preferred embodiment of the self-centering valvulotome of the present invention in the normal position.
Figure 3A:
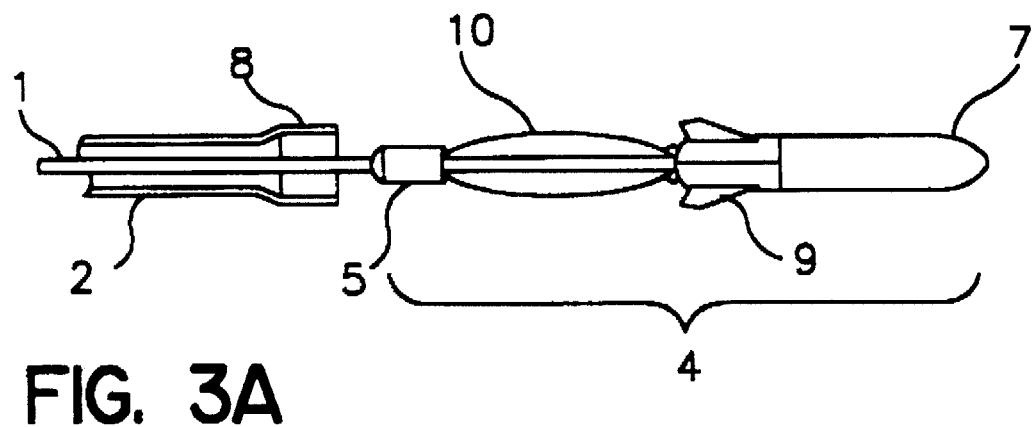
FIGS. 3A and 3B are side views of the cutting head of the FIG. 2 embodiment in both the normal and abandon positions of use thereof.
Figure 3B:
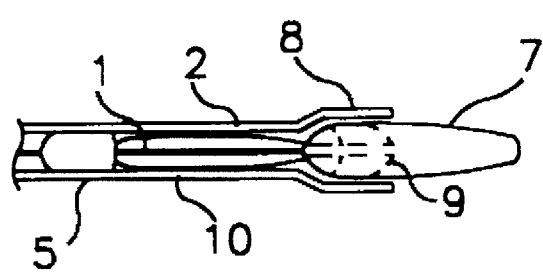
Figure 4A:
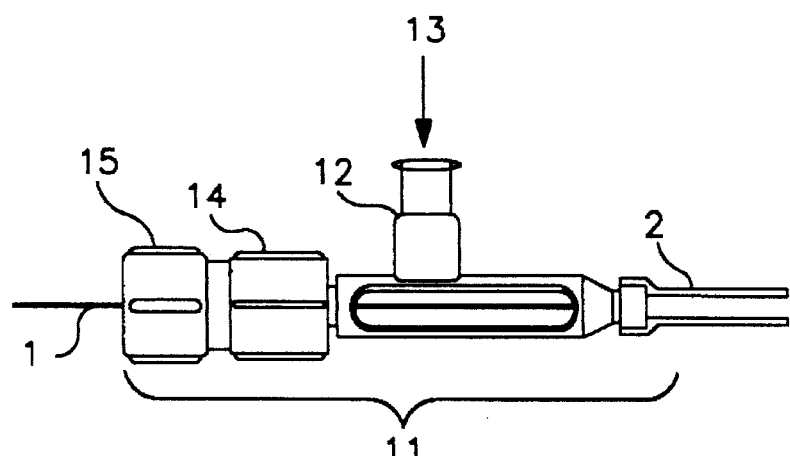
FIGS. 4A and 4B are side views of the control mechanism of the FIG. 2 embodiment in both the normal and abandon positions of use thereof.
Figure 4B:
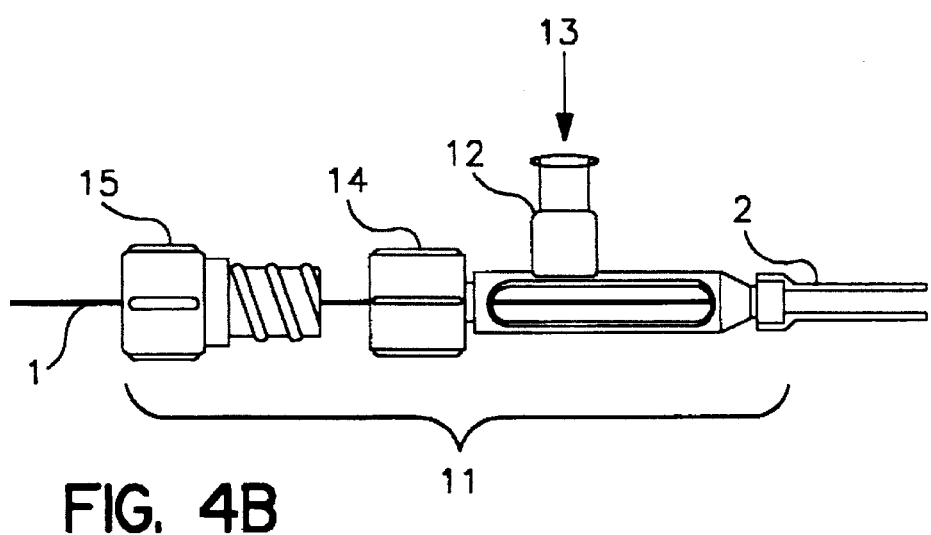
Figure 5:
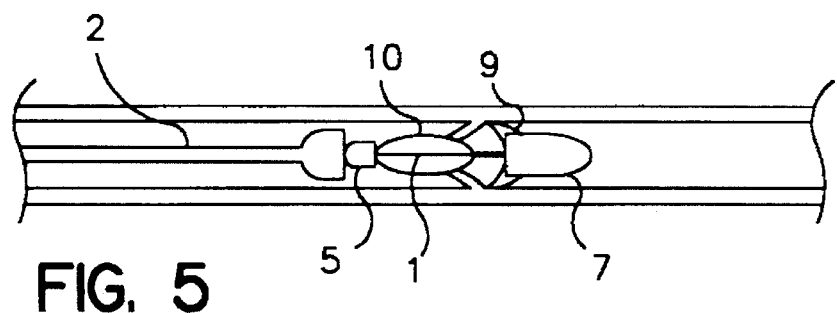
FIG. 5. is a diagrammatic view of the FIGS. 2–4 embodiment of the present invention disposed within a vein, as envisioned during use.

A self-centering valvulotome is provided. As may be seen in FIGS. 2 through 4B, the valvulotome of the present invention has a flexible cable 1 partly disposed within a protective sheath 2 having a lumen 3, both the flexible cable and the protective sheath each having a distal end and a proximal end. A cutting unit 4 is attached to the distal end of the flexible cable. The cutting unit has a base 5, at least three radially mounted, retractable cutting blades 6 attached to the base, and a tip 7 capable of accommodating the at least three radially mounted retractable cutting blades. The distal end of the protective sheath is flared outward sufficiently to accommodate the cutting unit.

Each retractable cutting blade comprises a free-floating, retractable cutting head 9 and a flat spring section 10 attached to the cutting unit base. The flat spring section of each retractable cutting blade 6 biases the cutting head against the venous wall. Each retractable cutting blade is formed from a blank by rotating the flat spring section until it is disposed at a 90° angle from the plane of the cutting head. The flat spring section is shaped so that the venous valve is opened upon insertion of the valvulotome cutting head, but that the vein's natural bloodflow is allowed to close the valve around the sheathed flexible cable once the cutting head has passed through. This feature maximizes the destruction of the valve flaps when the cutting head is withdrawn through the valve.

A dual-purpose control mechanism 11 is attached to the protective sheath's proximal end, allowing the passage therethrough of the flexible cable. The control mechanism comprises a T-valve segment 12, having an access port 13 and a terminal end 14, disposed partly within the proximal end of the protective sheath, the terminal end of the T-valve segment being adapted to allow engagement of a pull handle 15 affixed to the proximal end of the flexible cable 1. When the pull handle engages the terminal end of the T-valve segment, a fluid-tight seal is created, allowing the introduction of a diagnostic or therapeutic fluid to the distal end of the protective sheath 2 via the T-valve access port 13 and the lumen 3 of the protective sheath 2.

The present invention stands in contrast to the prior art valvulotome shown in FIG. 1 in several important ways. First, the present invention employs a multiplicity of cutting blades, thereby ensuring complete valve disablement. Further, the cutting blades are automatically biased against the venous wall and also self-center the device, thereby eliminating the need for surgeon control. Finally, the valvulotome of the present invention has a dual purpose control mechanism that allows the surgeon to sheath the cutting head if the need arises and also to monitor fluid pressure in a vessel or introduce fluid into or withdraw fluid from a vessel.

To measure the fluid pressure in a vessel, the surgeon first accesses the vessel in at least one point, inserts a valvulotome of the present invention into the vessel via the access point, feeds the valvulotome into the vein segment until the cutting unit is at the point where fluid pressure readings are desired; attaches a fluid pressure measurement device to the access port of the dual-purpose control unit's upper end; and measures the fluid pressure at the desired point.

To introduce fluid into or withdraw fluid from a vessel, the surgeon again first accesses the vessel in at least one point, inserts a valvulotome of the present invention into the vessel via the access point, feeds the valvulotome into the vessel until the cutting unit is at the point where fluid is desired to be added or withdrawn; and introduces a diagnostic or therapeutic fluid into the vessel at the distal end of the protective sheath via the access port of the dual-purpose control unit's upper end and the lumen of the protective sheath, or, alternatively, withdrawing fluid from the vessel through the distal end of the protective sheath via the lumen of the protective sheath and the access port of the dual-purpose control unit's upper end.

The valvulotome of the present invention may likewise be used in other, non-surgical applications that require a self-centering device. Accordingly, the presently claimed invention may be employed even if certain features of the embodiments described herein are omitted or substituted for.

The invention likewise may be embodied in other specified forms without departing from the spirit or essential characteristics thereof. The present embodiments are therefore to be considered in all respects as illustrative and not restrictive, and all changes which come within the meaning and range or equivalency of the claims are therefore intended to be embraced therein.

What is claimed is:

1. A self-sizing, self-centering valvulotome comprising:

(a) a protective sheath having a lumen, a flared distal end, and a proximal end;

(b) a flexible cable having a distal end and a proximal end and being partly and slidably disposed within the protective sheath;

(c) a self-sizing, self-centering cutting unit having a base, at least three retractable cutting members, each having a first, attached end equally radially mounted on the base, a second, unattached end defining a free-floating cutting blade, and a self-sizing, self-centering arm disposed therebetween, and a tip capable of accommodating the at least three radially mounted, retractable cutting blades, the self-sizing, self-centering cutting unit being attached to the cable's distal end such that the cutting unit is capable of slidably fitting within the flared distal end of the protective sheath such that it can be partially retracted within the protective sheath in a sheathed position and extended to an unsheathed position by means of the flexible cable, the base and the tip are separated by a distance not to exceed the length of the retractable cutting blades, each retractable cutting member being constructed so that the self-sizing, self-centering arm extends outward in a radial direction relative to the cable such that, in the unsheathed position, the radial distance separating the outermost point of each self-sizing, self-centering arm from the cable is greater than the radial distance separating the outermost point of each cutting blade from the cable, and each cutting blade having an upper, non-cutting outermost edge shielding a cutting edge disposed inwardly therefrom relative to the cable such that the cutting edge is oriented toward the proximal end of the cable; and (d) a dual-purpose control mechanism attached to the protective sheath's proximal end and allowing the passage therethrough of the flexible cable, such that the surgeon can sheathe and unsheathe the cutting head by sliding the flexible cable distally or proximally relative to the protective sheath.

2. The self-sizing, self-centering valvulotome, as claimed in claim 1, wherein each retractable cutting member is formed from a flat blank by rotating the cutting blade until it is disposed at about a 90° angle from the plane of the self-sizing, self-centering arm.

3. The self-centering valvulotome, as claimed in claim 1, wherein the self-sizing, self-centering arm is shaped so that the venous valve is opened upon insertion of the valvulotome cutting head, but that the vein's natural bloodflow is allowed to close the valve around the sheathed flexible cable once the cutting head has passed through.

4. The self-centering valvulotome, as claimed in claim 1, wherein the control mechanism comprises a T-valve segment having a terminal end and an upper end disposed at an angle of about 90° or less from the axis thereof, the T-valve segment being disposed partly within the proximal end of the protective sheath and the terminal end of the T-valve segment being adapted to allow engagement of a pull handle attached to the proximal end of the cable.

5. The self-centering valvulotome, as claimed in claim 4, wherein the upper end of the T-valve has an access port.

6. The self-centering valvulotome, as claimed in claim 5, wherein the pull handle engages the terminal end of the T-valve segment to create a fluid-tight seal, thereby allowing the introduction of a diagnostic or therapeutic fluid to the distal end of the protective sheath via the T-valve access port and the lumen of the protective sheath.

7. A self-sizing, self-centering valvulotome comprising:
   (a) protective sheathing means having a lumen, a distal end, and a proximal end;
   (b) means partly and slidably disposed within the protective sheathing means for transmitting linear motion;
   (c) self-sizing, self-centering means for cutting attached to the distal end of the motion transmitting means and drivable for cutting movement through said motion transmitting means; and
   (d) control means attached to the proximal end of the protective sheathing means and allowing the passage therethrough of the motion transmitting means such that the surgeon can sheathe and unsheathe the cutting means by sliding the motion transmitting means proximally or distally relative to the protective sheathing means,
   the self-sizing, self-centering means for cutting comprises a base means attached to the motion transmitting means, at least three retractable cutting member means equally radially disposed about the motion transmitting means, and a tip means capable of accommodating the at least three cutting member means, each cutting member means being constructed so that a first end is attached to the base means, a second end having a cutting blade means is not attached to the motion transmitting means, and a self-sizing, self-centering arm means connects the first and second ends and extends outward in a radial direction relative to the motion transmitting means, such that when the cutting means is in the unsheathed position the radial distance separating the outermost point of each self-sizing, self-centering arm means from the motion transmitting means is greater than the radial distance separating the outermost point of each cutting blade means from the motion transmitting means.

8. The self-sizing, self-centering valvulotome, as claimed in claim 7, wherein each retractable cutting member is formed from a flat blank by rotating the cutting blade means until it is disposed at about a 90° angle from the plane of the self-sizing, self-centering arm means.

9. The self-centering valvulotome, as claimed in claim 7, wherein the control means comprises a valve means having a terminal end, the valve means being disposed partly within the proximal end of the protective sheathing means and the terminal end of the valve means being adapted to allow engagement of a handle means attached to the proximal end of the flexible cable means.

10. The self-centering valvulotome, as claimed in claim 9, wherein the valve means has an access port means.

11. A self-centering valvulotome, as claimed in claim 10, wherein the handle means engages the terminal end of the valve means to create a fluid-tight seal, thereby allowing the introduction of a diagnostic or therapeutic fluid to the distal end of the protective sheathing means via the access port means and the lumen means of the protective sheathing means.

12. A cutting device with a self-centering capability for use within a tubular passageway, comprising, in combination:
   (a) a flexible cable having a distal end and a proximal end;
   (b) self-centering means for cutting;
   (c) means for attaching said means for cutting to said flexible cable;
   wherein the self-centering means for cutting is attached to the flexible cable via the means for attachment such that said means for attaching and said means for cutting are axially disposed with relation to said flexible cable, and further wherein the self-centering means for cutting is a unit that comprises a base means, at least three retractable cutting blade means attached to the base means and equally, radially disposed about the flexible cable, and a tip means capable of accommodating the retractable cutting blade means, the unit constructed such that the base means and the tip means are separated by a distance not to exceed the length of the retractable cutting blade means, each retractable cutting blade means being constructed so that it defines a first end suitable for attachment to the base means, a second end forming a cutting head means, and a self-sizing, self-centering arm means extending therebetween and outwardly in a radial direction relative to the cable such that, in the unsheathed position, the radial distance separating the outermost point of each self-sizing, self-centering arm from the cable is greater than the radial distance separating the outermost point of each cutting head from the cable.

13. The self-sizing, self-centering cutting device, as claimed in claim 12, wherein each retractable cutting blade means is formed from a flat blank by rotating the cutting blade means until it is disposed at about a 90° angle from the plane of the retractable self-sizing, self-centering arm means.

14. A method of preparing a vein for in situ arterial bypass surgery comprising:
   (a) selecting a suitable vein for the procedure;
   (b) accessing the vein at both a distal and a proximal point and segmenting it thusly;
   (c) inserting a valvulotome into the vein segment at its distal access point, wherein the valvulotome comprises:
      (i) a flexible cable having a distal end and a proximal end; and a cutting unit having a base, at least three equally radially mounted, retractable cutting blades attached to the base, and a tip capable of accommodating the at least three radially mounted retractable cutting blades, the cutting unit being attached to the cable's distal end such that the base and the tip are separated by a distance not to exceed the length of the retractable cutting blades, each retractable cutting blade being constructed so that it defines a cutting head and a self-sizing, self-centering arm extending outward in a radial direction relative to the cable such that the radial distance separating the outermost point of each self-sizing, self-centering arm from the cable is greater than the radial distance separating the outermost point of each cutting blade from the cable;

(d) feeding the valvulotome into the vein segment until the cutting unit is past the most proximal valve in the vein segment; and (e) withdrawing the valvulotome from the vein segment, thereby severing each valve in the segment.

15. A self-sizing, self-centering device for clearing a tubular passageway, comprising:

(a) a flexible cable having a distal end and a proximal end;

(b) a cutting unit having a base, at least three equally radially mounted retractable cutting blades attached to the base, and a tip capable of accommodating the at least three radially mounted retractable cutting blades, the cutting unit being attached to the cable's distal end such that the base and the tip are separated by a distance not to exceed the length of the retractable cutting blades, each retractable cutting blade being constructed so that it defines a cutting head and a self-sizing, self-centering arm extending outward in a radial direction relative to the cable such that the radial distance separating the outermost point of each self-sizing, self-centering arm from the cable is greater than the radial distance separating the outermost point of each cutting blade from the cable;

(c) a control mechanism attached to the flexible cable's proximal end such that the cutting unit can be inserted into or withdrawn from the tubular passageway to be cleared by means of the control mechanism.

16. The self-centering device for clearing a tubular passageway, as claimed in claim 15, wherein each retractable cutting member is formed from a flat blank by rotating the retractable cutting blade until it is disposed at about a 90° angle from the plane of the self-centering, self-sizing arm.

17. The device for clearing a tubular passageway, as claimed in claim 15, wherein the flexible cable is partly and slidably disposed within a protective sheath having a lumen, a distal end, and a proximal end.

* * * * *